United States Patent
Williams

(10) Patent No.: US 11,654,181 B2
(45) Date of Patent: May 23, 2023

(54) USE OF CXCL12 FOR THERAPY AFTER PROSTATE SURGERY

(71) Applicant: Wake Forest University Health Sciences, Winston-Salem, NC (US)

(72) Inventor: James K. Williams, Clemmons, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 3 days.

(21) Appl. No.: 16/637,498

(22) PCT Filed: Aug. 10, 2018

(86) PCT No.: PCT/US2018/046156
§ 371 (c)(1),
(2) Date: Feb. 7, 2020

(87) PCT Pub. No.: WO2019/032930
PCT Pub. Date: Feb. 14, 2019

(65) Prior Publication Data
US 2020/0215160 A1    Jul. 9, 2020

Related U.S. Application Data

(60) Provisional application No. 62/544,176, filed on Aug. 11, 2017.

(51) Int. Cl.
*A61K 38/19* (2006.01)
*A61P 15/10* (2006.01)
*A61K 9/00* (2006.01)
*A61K 48/00* (2006.01)

(52) U.S. Cl.
CPC .......... *A61K 38/195* (2013.01); *A61K 9/0019* (2013.01); *A61K 9/0031* (2013.01); *A61K 9/0034* (2013.01); *A61P 15/10* (2018.01); *A61K 48/00* (2013.01)

(58) Field of Classification Search
None
See application file for complete search history.

(56) References Cited

U.S. PATENT DOCUMENTS

| | | | |
|---|---|---|---|
| 5,385,561 A | 1/1995 | Cerny | |
| 5,588,960 A | 12/1996 | Edwards et al. | |
| 5,925,629 A | 7/1999 | Place | |
| 7,015,253 B2 | 3/2006 | Escandon et al. | |
| 7,598,028 B2 | 10/2009 | Macoska | |
| 7,662,392 B2 | 2/2010 | Itescu | |
| 7,939,057 B2 | 5/2011 | Battista et al. | |
| 8,435,953 B2 | 5/2013 | Tabata | |
| 8,513,007 B2 | 8/2013 | Penn et al. | |
| 8,513,213 B2 | 8/2013 | Penn et al. | |
| 10,420,818 B2 | 9/2019 | Williams | |
| 2009/0311223 A1* | 12/2009 | Ichim .................. | A61K 35/545 424/93.7 |
| 2010/0003297 A1 | 1/2010 | Tobias et al. | |
| 2015/0110853 A1 | 4/2015 | Ghanbari et al. | |
| 2017/0106050 A1 | 4/2017 | Williams | |

FOREIGN PATENT DOCUMENTS

| | | | |
|---|---|---|---|
| WO | WO 2007/149548 | * 12/2007 | |
| WO | WO 2015/171417 | * 11/2015 | ............. A61K 38/16 |
| WO | 2018/183625 | 10/2018 | |

OTHER PUBLICATIONS

Janssens et al., Cellular & Molecular Immunology (2018) 15, 299-311 (Year: 2018).*
Phillips, A., J Pharm Pharmacology, 2001; 53: 1169-1174 (Year: 2001).*
Winkler, Ther. Deliv. 2013; 4: 791-809 (Year: 2013).*
Jafarlou et al., Journal of Biological Regulators & Homeostatic Agents, 2016: 30: 315-321 (Year: 2016).*
Resnick et al., N Engl J Med 368;5, 2013 (Year: 2013).*
Montorsi et al., European Urology 48 (2005) 938-945 (Year: 2005).*
Bhattacharya et al., PLoS ONE 12(3): e0171355. https://doi.org/10.1371/journal.pone.0171355; 22 pages total (Year: 2017).*
Mitchell Steiner, Current Urology Reports 2000, 1:20-2 (Year: 2000).*
Herrera-Imbroda et al., Advanced Drug Delivery Reviews 82-83 (2015) 106-116 (Year: 2015).*
Yiou et al., Stem Cells 2016; 34:392-404; first published online Oct. 6, 2015 (Year: 2015).*
International Search Report and Written Opinion corresponding to PCT/US2018/046156, dated Feb. 14, 2018 (8 pp).
Haas et al. "The Worldwide Epidemiology of Prostate Cancer: Perspectives from Autopsy Studies" The Canadian Journal of Urology, 15(1):3866-3871 (2008).
Siegel et al. "Cancer Statistics, 2017" CA Cancer J Clin., 67(1):7-30 (2017).
Sooriakumaran et al. "Comparative effectiveness of radical prostatectomy and radiotherapy in prostate cancer: observational study of mortality outcomes" BMJ, 348:g1502 (2014) (13 pp).
Grasso et al. "Posterior musculofascial reconstruction after radical prostatectomy: an updated systematic review and meta-analysis" BJUI Int., 118(1):20-34 (2016).
Ficarra et al. "Systematic review and meta-analysis of studies reporting urinary continence recovery after robot-assisted radical prostatectomy" Eur. Urol., 62(3):405-417 (2012). Abstract.
Ficarra et al. "Systematic review and meta-analysis of studies reporting potency rates after robot-assisted radical prostatectomy" Eur. Urol., 62(3):418-430 (2012). Abstract.
D'Apuzzo et al. "The chemokine SDF-1, stromal cell-derived factor 1, attracts early stage B cell precursors via the chemokine receptor CXCR4" Eur. J. Immunol., 27(7):1788-1793 (1997). Abstract.

(Continued)

*Primary Examiner* — Christina M Borgeest
(74) *Attorney, Agent, or Firm* — Myers Bigel, P.A.

(57) ABSTRACT

This invention relates to C-X-C motif chemokine 12 (CXCL12), also known as stromal cell-derived factor 1 (SDF-1), vectors encoding the same, and methods of using the same for a male subject that has undergone prostate surgery to treat urological symptoms of the surgery.

16 Claims, No Drawings

(56) References Cited

OTHER PUBLICATIONS

Yiou et al. "Delivery of Human Mesenchymal Adipose-Derived Stem Cells Restores Multiple Urological Dysfunctions in a Rat Model Mimicking Radical Prostatectomy Damages Through Tissue-Specific Paracrine Mechanisms" Stem Cells, 34(2):392-404 (2016).
Jeon et al. "Combination Therapy Using Human Adipose-derived Stem Cells on the Cavernous Nerve and Low-energy Shockwaves on the Corpus Cavernosum in a Rat Model of Post-prostatectomy Erectile Dysfunction" Urology, 88:226, e1-9 (2016). Abstract.
Kaplan et al. "Social behavior and gender in biomedical investigations using monkeys: studies in atherogenesis" Laboratory Animal Science, 41(4):334-343 (1991). Abstract.
Ganzer et al. "Anatomical description of the periprostatic nerves in the male rhesus monkey (Macaca mulatta)" World Journal of Urology, 29(3): 375-380 (2011).
Ganzer et al. "Is the rhesus monkey (Macaca mulatta) comparable to humans? Histomorphology of the sphincteric musculature of the lower urinary tract including 3D-reconstruction" Anat. Histol. Embryol., 33(6):355-361 (2004). Abstract.
Gratzke et al. "Effects of Long-Term Dietary Soy Treatment on Female Urethral Morphology and Function in Ovariectomized Nonhuman Primates" J. Urol., 180(5):2247-2253 (2008). Abstract.
Crivellaro et al. "Systematic review of surgical treatment of post radical prostatectomy stress urinary incontinence" Neurourol Urodyn. 35(8): 875-881 (2016). Abstract.
Sakao et al. "CXCR4 Is a Novel Target of Cancer Chemopreventative Isothiocyanates in Prostate Cancer Cells" Cancer Prev. Res. 8(5):365-374 (2015).
Gupta et al. "Role of stromal cell-derived factor 1a pathway in bone metastatic prostate cancer" The Journal of Biomedical Research, 30(3):181-185 (2016).
Sun et al. "Expression of CXCR4 and CXCL12 (SDF-1) in human prostate cancers (PCa) in vivo" J. Cell Biochem., 89(3): 462-473 (2003). Abstract.
Mangir et al. "Stem cell therapies in post-prostatectomy erectile dysfunction: A critical review" The Canadian Journal of Urology, 24(1):8609-8619 (2017).

\* cited by examiner

USE OF CXCL12 FOR THERAPY AFTER PROSTATE SURGERY

CROSS REFERENCE TO RELATED APPLICATIONS

This application is a 35 U.S.C. § 371 national phase application of International Application Serial No. PCT/US2018/046156, filed Aug. 10, 2018, which claims the benefit of U.S. provisional patent application Ser. No. 62/544,176, filed Aug. 11, 2017, the disclosure of which is incorporated by reference herein in its entirety.

STATEMENT OF GOVERNMENT SUPPORT

This invention was made with Government support under grant number R01 DK 083688 awarded by the National Institutes of Health. The Government has certain rights to this invention.

BACKGROUND

Prostate cancer is the leading cause of cancer among men in the United States, with 161,360 estimated new diagnoses, and it is the third leading cause of cancer death, with an estimated 26,730 men dying from the disease in 2017 (Siegel R L, Miller K D, Jemal A. Cancer Statistics, 2017. CA Cancer J Clin. 2017; 67(1): 7). For most men with localized prostate cancer, radical prostatectomy provides excellent long-term oncologic outcomes and, therefore, remains the gold standard treatment (Haas G P, Delongchamps N, Brawley O W, et al. The worldwide epidemiology of prostate cancer: perspectives from autopsy studies. Can J Urol. 2008; 15(1): 3866; Sooriakumaran P, Nyberg T, Akre O. Comparative effectiveness of radical prostatectomy and radiotherapy in prostate cancer: observational study of mortality outcomes. BMJ. 2014; 348: 1502; Grasso A A C, Mistretta F A, Sandri M, et al. Posterior musculofascial reconstruction after radical prostatectomy: an updated systematic review and meta-analysis. BJUI. 2016; 118(1): 20). Although nerve sparing prostatectomies, including robotic surgery, are currently available for many patients; persistent urinary incontinence (UI) occurs in 4-31% of patients, and erectile dysfunction (ED) occurs in 54-90% at 12 months post prostatectomy (Ficarra V, Novara G, Rosen R C, Artibani W, et al. Systematic review and meta-analysis of studies reporting urinary continence recovery after robot-assisted radical prostatectomy. Eur Urol. 2012 62(3): 405; Ficarra V, Novara G, Ahlering T E, et al. Systematic review and meta-analysis of studies reporting potency rates after robot-assisted radical prostatectomy. Eur Urol. 2012; 62(3): 418. These represent significant problems impacting quality of life for patients, and better treatment options are needed.

Current therapeutic options include the use of phosphodiesterase 5 inhibitors therapy, vacuum erectile devices, intraurethral suppositories with alprostadil and intracavernosal injections, and stem cells. However, these therapies are only partially effective and may require repeated procedures. Alternate therapies are needed.

SUMMARY

Provided herein is a method of treating a male subject, wherein said subject has undergone prostate surgery, for urological symptoms from the surgery, said method comprising administering CXCL12 to the subject in a treatment-effective amount.

In some embodiments, the surgery is prostatectomy such as radical prostatectomy.

In some embodiments, the administering is carried out by administering CXCL12 in the periurethral space of the subject.

In some embodiments, the administering is carried out by locally administering CXCL12 at one or more sites at or near the site of the prostate surgery.

In some embodiments, the CXCL12 is administered within a time frame of from one month to six months after said prostate surgery.

Also provided is CXCL12 or a vector encoding CXCL12 as described herein for use in carrying out a method as described herein, or for use in the preparation of a medicament for carrying out a method as described herein.

DETAILED DESCRIPTION

The present invention is primarily concerned with the treatment of male subjects, such as human male subjects, but the invention may also be carried out on animal subjects, particularly mammalian subjects such as non-human primates, dogs, cats, livestock and horses for veterinary or research purposes.

"Treat" as used herein refers to any type of treatment that imparts a benefit to a patient, particularly reducing or ameliorating severity of a symptom as described herein, delaying or retarding progression or worsening of a symptom or disorder as described herein, etc.

"Pharmaceutically acceptable" as used herein means that the compound or composition is suitable for administration to a subject to achieve the treatments described herein, without unduly deleterious side effects in light of the severity of the disease and necessity of the treatment.

1. Active Compounds.

The active compound used herein is the C-X-C motif chemokine 12 (CXCL12), also known as chemokine protein stromal cell-derived factor 1 (SDF-1). In humans, it is encoded by the CXCL12 gene. CXCL12 is known and described in, for example, M. D'Apuzzo et al., The chemokine SDF-1, stromal cell-derived factor 1, attracts early stage B cell precursors via the chemokine receptor CXCR4, Eur. J. Immunol. 27, 1788-1793 (1997); Y. Tabata, U.S. Pat. No. 8,435,953, and Penn et al., U.S. Pat. Nos. 8,513,213 and 8,513,007; and S. Itescu, U.S. Pat. No. 7,662,392, the disclosures of which are incorporated by reference herein in their entirety.

CXCL12 used in the present invention may be that of a human, a non-human primate or other mammal. In some embodiments, the CXCL12 is recombinant CXCL12. As used herein, CXCL12 may include isoforms and mature forms. See U.S. Pat. No. 8,435,953 to Tabata. In addition, as long as CXCL12 has activity as a chemokine, CXCL12 may be substituted, deleted and/or added by one or plural amino acid(s) in the amino acid sequence. Similarly, it may be substituted, deleted and/or added by sugar chain.

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

CXCL12 may form a salt (preferably, an acid addition salt) with a physiologically acceptable acid (for example, an inorganic acid or an organic acid) or a base (for example, an alkali metal salt). Examples of the salt include a salt with an inorganic acid (for example, hydrochloric acid, phosphoric acid, hydrobromic acid, or sulfuric acid) and a salt with an organic acid (for example, acetic acid, formic acid, propionic acid, fumaric acid, maleic acid, succinic acid, tartaric acid, citric acid, malic acid, oxalic acid, benzoic acid, methanesulfonic acid, or benzenesulfonic acid).

In the present invention, CXCL12 may be purified to a level at which the action of CXCL12 is not inhibited by other contaminants. Preferably, CXCL12 may be purified to be usable as a pharmaceutical preparation.

2. Pharmaceutical Formulations.

The active compounds described above may be formulated for administration in a pharmaceutical carrier in accordance with known techniques. See, e.g., Remington, *The Science And Practice of Pharmacy* (9$^{th}$ Ed. 1995). Formulations of the present invention suitable for parenteral administration comprise sterile aqueous and non-aqueous injection solutions of the active compound(s), which preparations are preferably isotonic with the blood of the intended recipient (e.g., saline). These preparations may contain anti-oxidants, buffers, bacteriostats and solutes which render the formulation isotonic with the blood of the intended recipient. Aqueous and non-aqueous sterile suspensions may include suspending agents and thickening agents.

The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules or tablets. For example, in one aspect of the present invention, there is provided an injectable, stable, sterile composition comprising an active compound(s), or a salt thereof, in a unit dosage form in a sealed container. The compound or salt may be provided in the form of a lyophilizate which is capable of being reconstituted with a suitable pharmaceutically acceptable carrier to form a liquid composition suitable for injection thereof into a subject.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In some embodiments, CXCL12 may be provided as a sustained release composition, such as a composition comprising CXCL12 and a hydrogel containing modified gelatin having a carboxyl group and/or a sulfo group. See U.S. Pat. No. 8,435,953 to Tabata.

3. Dosage and Routes of Administration.

As noted above, the present invention provides pharmaceutical formulations comprising the CXCL12 (including pharmaceutically acceptable salts thereof), in pharmaceutically acceptable carriers for parenteral administration.

In some embodiments, CXCL12 is administered into the periurethral space of the subject, such as at one or more sites at or near the site of the prostate surgery. For example, administering may be injection of CXCL12 at one or more sites in the periurethral space at the level of the vesiculourethral anastomosis for a patient having undergone radical prostatectomy.

Translumenal injection (e.g., transurethral or trans-rectal injection) may be carried out by any suitable technique, including but not limited to those described in U.S. Pat. Nos. 7,015,253; 5,925,629; 5,588,960; and 5,385,561, and US Patent Application Publication No. US2010/0003297A1 by Tobias et al. (MIT), the disclosures of which are incorporated herein by reference in their entirety.

The pharmaceutical carrier for injection may optionally include a viscosity-enhancing agent (e.g., cellulose derivatives, alginic acid derivatives, dextrans, gelatine, collagen, hyaluronic acids, etc.) preferably type 1 collagen (e.g., CONTIGEN® collagen), the viscosity-enhancing agent included in an amount sufficient to (a) reduce potential leakage of the formulation from the injection site, and/or (b) further treat the incontinence.

The therapeutically effective dosage of any specific compound, the use of which is in the scope of present invention, will vary somewhat from compound to compound, and patient to patient, and will depend upon the condition of the patient and the route of delivery. In general, for periurethral administration of CXCL12, an amount of from about 50, 100, 125 or 150 to 500, 700, or 800 nanograms; or from 1, 5 or 10 micrograms to 50, 100 or 500 micrograms per injection may be appropriate. The subject may receive, e.g., one injection per treatment session, or a plurality of injections (e.g., 2, 3, 4, 5, 6) into the periurethral space at different sites therein (e.g., sites distributed circumferentially around a vesiculo-urethral anastomosis) in each treatment session.

The CXCL12 may be administered directly, e.g., by injection, or by administering (e.g., by injection) a nucleic acid vector (e.g., integrating and non-integrating viral vectors, retroviral vectors, plasmid vectors, linear DNA vectors, etc.) that encodes CXCL12 and expresses (e.g., transiently or constitutively expresses) CXCL12 in the patient's tissue. Suitable vectors, including plasmid vectors, are known or will be apparent to those skilled in the art based on the present disclosure and include but are not limited to the plasmid deposited with the American Type Culture Collection under accession number PTA-13320, as described in, for example, Penn et al., U.S. Pat. Nos. 8,513,213 and 8,513,007, the disclosures of which are incorporated by reference herein.

In some embodiments, CXCL12 is administered once, or multiple times, in the days, weeks, months, or years after a surgery, e.g., radical prostatectomy. In some embodiments, CXCL12 is administered 5, 6, or 7 weeks after surgery. In some embodiments, CXCL12 is administered 5, 6 or 7 months after surgery. In some embodiments, CXCL12 is administered 1 day, 2 days, 3, days, 4 days, 5 days, 6 days, 7 days or later after surgery. In some embodiments, CXCL12 is administered 1 week, 2 weeks, 3 weeks, 4 weeks, 5 weeks, 6 weeks, 7 weeks, 8 weeks or later after surgery. In some embodiments, CXCL12 is administered 1 month, 2 months, 3 months, 4 months, 5 months, 6 months, 7 months, 8 months, 9 months, 10 months, 11 months, 12 months or later after surgery. In some embodiments, CXCL12 is administered 1 year after surgery. In some embodiments, CXCL12 is administered 1 year, 2 years, 3 years, 4 years, 5 years, 6 years, or later after surgery.

If desired, treatment sessions may be repeated periodically as needed (e.g., once every two or four months). Where a nucleic acid vector is administered, the vector can be administered in an amount effective to achieve corresponding levels of expression of the CXCL12 in the injection site. However, in some embodiments, only a single injection is administered.

The present invention is explained in greater detail in the following non-limiting Examples.

Example 1

In Vivo Evaluation of CXCL12 Administration in Primate Model of Radical Prostatectomy Autologous stem cell injection has been tested in experimental studies using rats (Yiou et al. Stem Cells. 2016; 34(2): 392-404; Jeon et al. Urology. 2016; 88:226, e1-9). However, rodents are known to readily regenerate tissues without treatment, thus making them problematic animal models for persistent ED and UI.

Cynomolgus monkeys share with human beings a similar genitourinary anatomy and physiology, including the risk for age associated diseases (Kaplan et al., Social behavior and gender in biomedical investigations using monkeys: studies in atherogenesis. Lab Anim Sci. 1991; 41(4): 334; Ganzer et al., Anatomical description of the periprostatic nerves in the male rhesus monkey (Macaca mulatta). World J Urol. 2011; 29(3): 375; Ganzer et al., Is the rhesus monkey (Macaca mulatta) comparable to humans? Histomorphology of the sphincteric musculature of the lower urinary tract including 3D-reconstruction. Anat Histol Embryol. 2004; 33(6): 355; Gratzke et al., Effects of long-term soy treatment on female urethral morphology and function in ovariectomized non-human primates. J Urol 2008; 180: 2247). A male cynomolgus monkey model of persistent post prostatectomy-induced urinary incontinence (UI) and erectile dysfunction (ED) was created and characterized, and the effect of local CXCL12 injection on these conditions was measured.

Materials and Methods.

Animal Model. Ten male (15 to 25 years of age) cynomolgus monkeys (Macaca fascicularis) weighing 6 to 9 Kg were purchased from certified commercial sources. The age ratio between cynomolgus monkeys and human beings is 1:3, which means that our monkey model is the age equivalent of 45-75 year old men. All procedures were previously approved by the Wake Forest University Institutional Animal Care and Use Committee, and done in compliance with the Animal Welfare Act and the Guide for Care and Use of Laboratory Animals. We also have in house environmental enrichment experts that customize and optimize the psychosocial living conditions for each monkey. All animals were euthanized according to American Veterinary Medical Association guidelines.

Study Design. Ten adult male cynomolgus monkeys were used; two for the study of normal pelvic anatomy. Eight animals were evaluated for sexual behavior and abdominal leak point pressures (ALPP) pre- and 6 months post-prostatectomy. Five animals were necropsied for tissue evaluation 6 months post-surgery. The other three animals received trans-rectal ultrasound-guided injection of CXCL12 into the peri-urethral space 6 weeks following the prostatectomy and were evaluated for up to 4 months.

Open Radical Retropubic Prostatectomy. Eight monkeys were sedated with ketamine 10 to 15 mg/Kg intramuscularly and 1% to 5% isoflurane was used to induce and maintain anesthesia. The surgical field was prepared in a sterile-fashion and a 5-French Foley catheter was placed into the urethra. A 3-4 cm lower midline abdominal incision was made to expose the extra-peritoneal retro-pubic space and bladder. The endopelvic fascia was approached using a gentle dissection of connective tissue ventrally and laterally to the bladder and then opened bilaterally. Bladder neck (which is more mobile in the NHP than in human beings) was isolated and opened proximally to the prostate, exposing the ampulla of the vas deferens and seminal vesicles. Then, the vasa deferentia on both sides were sectioned and cauterized bilaterally. Right and left seminal vesicles (which are relatively larger in these NHPs than in human beings) were dissected from the perirectal fat and both vascular pedicles controlled with hemostatic clips. Subsequently, the dorsal vascular complex (DVC) was approached and cauterized with bipolar electro-cautery. Following DVC control, prostate apex was dissected and the membranous urethra transected sharply distally to the apex. Ultimately, both prostatic lateral pedicles were controlled and the specimen was removed. After a careful hemostasis, a new 5-French Foley catheter was placed, and four sutures (3/6/9/12 o'clock) were placed to anastomose bladder and membranous urethra. Extravasation was observed after infusion of 10 ml of saline through the Foley catheter. A Jackson-Pratt (JP) drain was placed and abdominal wall closed. The JP drain was removed on 3rd day and Foley catheter on 14th day after surgery. The surgery team was led by a physician who has over 3 decades of experience performing radical prostatectomies in open as well as robotic approaches.

Injection of CXCL12. In each side of the urethra, 1 ml of saline containing 125 ng of human recombinant CXCL12 was injected in the periurethral space at the level of vesiculo-urethral anastomosis. The injection was delivered trans-rectally using ultrasound guidance in anesthetized monkeys that had received an enema. The dose of 125 ng CXCL12 was based on a previous study in female monkeys.

Urodynamic Study. Animals were sedated with ketamine 10 to 15 mg/kg intramuscularly and 1% to 5% isoflurane was used to induce and maintain anesthesia. Urodynamic studies (UDS) were performed under general anesthesia using Goby IV—Goby Wireless Urodynamics System from Laborie (Williston, Vt.) in three time-points: baseline, 3 and 6 months postoperative. The intra-vesical pressure was measured with 6-French nasogastric tube connected to the transducer and abdominal pressure was measured with 7-French TDOC abdominal catheter placed into the distal rectum proximally to the anal sphincter. Bladder was filled at 5 ml/min with warmed 0.9% sodium chloride and methylene blue solution. The first filling was performed to measure the bladder compliance and maximum cystometric capacity (MCC) as well as to evaluate detrusor over-activity. The MCC was estimated when urinary leakage came out through the urethra in the absence of Valsalva or detrusor over-activity. Abdominal leak point pressure (ALPP) was measured at 50% MCC without the intra-vesical catheter. Each measurement was repeated three times.

Statistical analysis. The statistical analyses were performed using RStudio software for Windows (R-Tools Technology Inc., Richmond Hill, ON, Canada). Statistical significance was set at p<0.05. For the primary aim, which was to develop a reproducible model of NHP radical prostatectomy, no statistical analysis was done. For ALPP data the group means were compared using a one-way ANOVA. The means were found to be significantly different and pairwise t-tests using the Holm-Bonferroni adjustment were used to compare individual group means. For the ICP data the group means of the "post" measurements were compared using one-way ANOVA.

Results

Pelvic Anatomy. Like human beings, cynomolgus males have an intra-pelvic bladder and urinary sphincter. The prostate, seminal vesicles and rectum are also positioned similar to that of human males.

Effects of Prostatectomy on Histology. Six months post-surgery, the anastomotic site of non-treated is somewhat smaller than the urethra above and below the anastomosis. There was significant fibrosis at the site in all untreated animals, with relative increases in collagen and reductions in muscle content.

Effects of CXCL12 Treatment on Histology. Six weeks following radical prostatectomy, CXCL12 was injected into the periurethral space using a transrectal approach. Two months following the injection, the vesiculo-urethral anastomosis was still fibrotic, but muscle fibers were beginning re-appear.

Erectile Dysfunction. Sexual behavior was monitored at three time points: baseline, 3, and 6 months postoperative. Prostatectomy reduced the ability of the monkeys to achieve erection and their attempts at mating. In the three monkeys receiving CXCL12 injections, the ability to achieve erection was either completely or partially restored.

Urodynamic Measures (Table 1). Prostatectomy reduced, and CXCL12 restored, leak point pressure (LPP) values. Following prostatectomy, LPP values remain low for at least 6 months. Table 1 shows maximal bladder capacity (MCC), compliance, and abdominal leak point pressures (ALPP) in 3 animals at baseline, after the open radical prostatectomy (ORP) and 1 month post CXCL12 injection.

TABLE 1

| | Before ORP | Before CXCL12 (4 weeks post ORP) | 1 month post CXCL12 |
|---|---|---|---|
| MCC (ml) | 50 ± 10 | 50 ± 15 | 50 ± 15 |
| Compliance (ml/cm $H_2O$) | 25 ± 7 | 22 ± 5 | 23 ± 5 |
| ALPP (cm $H_2O$) | 80 ± 20 | 15 ± 5 | 50 ± 7 |

Discussion

In this study, a non-human primate model of persistent erectile and urinary dysfunction after open radical prostatectomy was characterized. Additionally, the efficacy of the chemokine CXCL12 to treat these conditions was tested. The major outcomes of the prostatectomy procedure in these monkeys were: 1) it was feasible and created an intact collagen rich urethrovesical anastomosis; 2) produced sustained and marked decrease in mating success; 3) produced sustained reduction in abdominal leak point pressures (ALPP); and 4) injection of CXCL12 restored urinary and erectile function in the few monkeys it was tested.

There are many similarities in gross anatomy of the distal urogenital tract between male cynomolgus monkeys and human males. However, there are some differences, including a more mobile bladder neck in the monkeys, making the surgery somewhat easier. The bladder neck in the monkeys is easily mobilized and can be dissected without major difficulties. Both vasa deferentia are located just beneath the bladder neck; seminal vesicles are larger than in humans and extend from the base of the prostate to the bladder dome; anterior prostate is composed of a thin tissue layer. It is unclear if these differences have any effects on the nerve/vascular damage due to the open prostatectomy between this species and human beings.

Slight differences in urogenital anatomy and innervation may have some bearing in the development of a NHP model of post nerve-sparing prostatectomy. Nevertheless, the size of the NHPs may permit development of newer surgical techniques that can lessen post-prostatectomy side-effects. Regardless, our goal was to first develop a model of persistent dysfunction to create a basis for therapeutic interventions using a regenerative medicine approach. The changes in the urodynamic measures and sexual function persisted for 6 months post-surgery (equivalent to 18 months in human terms), thus creating a stable platform for testing treatment options.

CXCL12 was chosen as the treatment chemokine because CXCL12 (sometimes referred to as SDF-1) plays a major role in cell trafficking and homing of progenitor cells to sites of injury. This is produced through a receptor (CXCR4) mechanism and enhances cell survival once at the injury site (Crivellaro et al., Systematic review of surgical treatment of post-radical prostatectomy stress urinary incontinence. Neurourol Urodyn. 2016; 35(8): 875). During injury, cells from the injured organ highly express CXCL12, which causes an increase of localized CXCL12 levels, and peripheral and bone marrow progenitor cells follow the chemical gradient to the organ (Ganzer et al., Anatomical description of the periprostatic nerves in the male rhesus monkey (Macaca mulatta). World J Urol. 2011; 29(3): 375; Ganzer et al., Is the rhesus monkey (Macaca mulatta) comparable to humans? Histomorphology of the sphincteric musculature of the lower urinary tract including 3D-reconstruction. Anat Histol Embryol. 2004; 33(6): 355).

There is some evidence that the CXCL12/CXCR4 signaling pathway may be involved in metastatic prostate cancer progression. Prostate cancer cells isolated from bone metastasis had overexpression of CXCR4 and CXCR7 chemokine receptors. (Sakao et al., Cancer Prev Res. 2015; 8(5):365-74; Gupta et al. J Biomed Res. 2016; 30(3):181-5). Analysis of CXCR4 expression in humans using high density microarrays from a cohort of 600 patients demonstrated elevated levels of this chemokine receptor in metastatic prostate cancer (Sun et al. J Cell Biochem. 2003; 89: 462-73). Though the long-term risk and benefits of CXCL12 and prostate cancer are not confirmed, due to its short half-life, the low dose of CXCL12 (125 ng) delivered as a single injection weeks after the surgical procedure may be a harmless and minimally invasive treatment for these patients.

Example 2

Experiments are performed as described above in a cohort of 15 adult male cynomolgus monkeys. The monkeys are 15-18 years of age to model 50-60 year old men, a common time of life men may require a prostatectomy. They are assigned to 1 of 3 treatment conditions: 1) no open radical prostatectomy, 2) open radical prostatectomy followed by a 100-125 ng CXCL12 injection 6 weeks after surgery, or 3) open radical prostatectomy followed by a 100-125 ng CXCL12 injection 6 months after surgery. All groups are analyzed for the parameters described above at 1, 3, and 6 months after CXCL12 treatment or equivalent time frame for the non-treated control group.

The foregoing is illustrative of the present invention, and is not to be construed as limiting thereof. The invention is defined by the following claims, with equivalents of the claims to be included therein.

What is claimed is:

1. A method of treating a male subject that has undergone prostate surgery for urological symptoms from the surgery, said method comprising administering wild-type CXCL12 protein to the subject in a treatment-effective amount,
    wherein said symptoms comprise erectile dysfunction,
    wherein said CXCL12 protein is administered within a time frame of from one month to six months after said prostate surgery, and
    wherein the administering is carried out by locally administering the CXCL12 protein at two or more sites at or near the site of the prostate surgery.

2. The method of claim 1, wherein said symptoms further comprise urinary incontinence.

3. The method of claim 1, wherein said subject is a human male subject.

4. The method of claim 1, wherein said surgery is prostatectomy.

5. The method of claim 1, wherein the prostate surgery is radical prostatectomy with a vesiculo-urethral anastomosis, and the administering is carried out by locally administering the CXCL12 protein at two or more sites in the periurethral space at the level of the vesiculo-urethral anastomosis.

6. The method of claim 1, wherein said administering is carried out by injecting said CXCL12 protein.

7. The method of claim 6, wherein the injecting is by transluminal injection.

8. The method of claim 6, wherein the injecting is carried out at a plurality of sites in the periurethral space.

9. The method of claim 6, wherein the injecting is by transurethral or transrectal injection.

10. The method of claim 1, wherein said CXCL12 protein is human CXCL12.

11. The method of claim 1, wherein said wild-type CXCL12 protein is formulated for administration in a pharmaceutical carrier.

12. The method of claim 1, wherein said surgery is radical prostatectomy.

13. A method of treating a male subject that has undergone prostate surgery for urological symptoms from the surgery, said method comprising administering wild-type CXCL12 protein to the subject in a treatment-effective amount,
    wherein said symptoms comprise erectile dysfunction,
    wherein said CXCL12 protein is administered within a time frame of from one month to six months after said prostate surgery,
    wherein the administering is carried out by locally administering the CXCL12 protein at one or more sites at or near the site of the prostate surgery, and
    wherein the prostate surgery is radical prostatectomy with a vesiculo-urethral anastomosis, and the administering is carried out by locally administering the CXCL12 protein at one or more sites in the periurethral space at the level of the vesiculo-urethral anastomosis.

14. The method of claim 13, wherein said CXCL12 protein is human CXCL12.

15. A method of treating a male subject that has undergone prostate surgery for urological symptoms from the surgery, said method comprising administering wild-type CXCL12 protein to the subject in a treatment-effective amount,
    wherein said symptoms comprise erectile dysfunction,
    wherein said CXCL12 protein is administered within a time frame of from one month to six months after said prostate surgery,
    wherein the administering is carried out by locally administering the CXCL12 protein at or near the site of the prostate surgery,
    wherein said administering is carried out by injecting said CXCL12 protein, and
    wherein the injecting is carried out at a plurality of sites in the periurethral space.

16. The method of claim 15, wherein said CXCL12 protein is human CXCL12.

* * * * *